(12) United States Patent
Hoerl et al.

(10) Patent No.: US 9,375,658 B2
(45) Date of Patent: Jun. 28, 2016

(54) POLYSACCHARIDE MATRIX HAVING A GRAFTED POLYMER, METHOD FOR PRODUCING THE SAME AND USE THEREOF

(75) Inventors: Hans-Heinrich Hoerl, Bovenden (DE); Wolfgang Demmer, Goettingen (DE); Rene Faber, Goettingen (DE); Christian Brumm, Witzenhausen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 1045 days.

(21) Appl. No.: 13/321,053

(22) PCT Filed: Apr. 23, 2010

(86) PCT No.: PCT/EP2010/002496
§ 371 (c)(1),
(2), (4) Date: Nov. 17, 2011

(87) PCT Pub. No.: WO2010/142363
PCT Pub. Date: Dec. 16, 2010

(65) Prior Publication Data
US 2012/0074068 A1 Mar. 29, 2012

(30) Foreign Application Priority Data

Jun. 13, 2009 (DE) .......................... 10 2009 024 824
Dec. 11, 2009 (DE) .......................... 10 2009 057 993

(51) Int. Cl.
*B01D 39/00* (2006.01)
*B01D 39/14* (2006.01)
(Continued)

(52) U.S. Cl.
CPC ............ *B01D 15/36* (2013.01); *B01D 67/0093* (2013.01); *B01D 71/16* (2013.01);
(Continued)

(58) Field of Classification Search
CPC ............... B01D 15/36; B01D 2323/38; B01D 67/0093; B01D 71/12; B01D 38/18; C08J 9/00; C08F 251/00

USPC ............ 210/500.29–500.33, 500.35, 500.27, 210/490; 264/48
See application file for complete search history.

(56) References Cited

U.S. PATENT DOCUMENTS 3,723,306 A * 3/1973 Bridgeford .................... 210/638
4,308,254 A 12/1981 Tayot et al.
(Continued)

FOREIGN PATENT DOCUMENTS

CA       1249952       2/1989
DE       28 40 503     11/1984
(Continued)

OTHER PUBLICATIONS

PCT/ISA/237, Apr. 2007.*
(Continued)

*Primary Examiner* — Ana Fortuna
(74) *Attorney, Agent, or Firm* — Gerald E. Hespos; Michael J. Porco; Matthew T. Hespos (57) ABSTRACT

A porous, non-particulate, convectively permeable polysaccharide matrix has a surface on which there is fixed a grafted-on polymer derived from at least one ethylenic monomer compound having functional groups, wherein the polysaccharide matrix is prepared by grafting a porous, non-particulate, convectively permeable polysaccharide starting matrix with the at least one ethylenic monomer compound in the presence of an organic acid having at least one carboxylic acid group and/or at least one acidic XH group, where X=—O, —S, or —N, and of a transition metal or lanthanide compound. The polysaccharide matrix has a high protein binding capacity. A process for preparing the polysaccharide matrix and a method for using the polysaccharide matrix for material separation also are provided.

19 Claims, 1 Drawing Sheet

(51) Int. Cl.
- *B01D 15/36* (2006.01)
- *B01D 67/00* (2006.01)
- *B01D 71/16* (2006.01)
- *C07K 1/18* (2006.01)
- *C08F 251/00* (2006.01)
- *C08J 7/14* (2006.01)
- *B01J 39/20* (2006.01)
- *B01J 20/32* (2006.01)

(52) U.S. Cl.
CPC ............ *B01J 20/3278* (2013.01); *B01J 39/20* (2013.01); *C07K 1/18* (2013.01); *C08F 251/00* (2013.01); *C08J 7/14* (2013.01); *B01D 2323/38* (2013.01); *B01D 2325/14* (2013.01); *B01D 2325/16* (2013.01)

(56) References Cited

U.S. PATENT DOCUMENTS

| | | | |
|---|---|---|---|
| 4,791,063 A | | 12/1988 | Hou et al. |
| 4,877,528 A | * | 10/1989 | Friesen et al. ........... 210/500.29 |
| 5,137,633 A | * | 8/1992 | Wang ........................... 210/490 |
| 5,215,692 A | | 6/1993 | Hoerl et al. |
| 2008/0090984 A1 | * | 4/2008 | Namikoshi et al. ........... 527/300 |

FOREIGN PATENT DOCUMENTS

| | | |
|---|---|---|
| DE | 39 29 648 | 11/1990 |
| EP | 0 337 144 | 10/1989 |
| EP | 0 490 940 | 5/1995 |
| EP | 0 538 315 | 12/1995 |
| EP | 0 722 360 | 6/1997 |
| EP | 0 527 992 | 2/1998 |
| EP | 0 921 855 | 11/2003 |
| EP | 1 163 045 | 6/2004 |
| EP | 1 614 459 | 7/2007 |
| EP | 1 718 668 | 8/2009 |
| EP | 1 386 660 | 9/2009 |
| WO | 92/00805 | 1/1992 |

OTHER PUBLICATIONS

"Synthesis of poly(acrylamide)-starch and hydrolyzed starch graft copolymers as a size base material for cotton textiles"—Mostafa Kh. M.—Polymer Degradation and Stability—Jan. 1997, pp. 125-130.

"Improvement of Blood Compatibility on Cellulose Dialysis Membrane"—Kazuhiko Ishihara et al.—Biomaterials—Jan. 1992—pp. 145-149.

"Graft-Copolymerization of Glycidyl Methacrylate onto Cotton Cellulose"—Shukla S. R et al.—Journal of Applied Polymer Science Oct. 17, 1994—pp. 279-288.

"Synthesis and Physiocochemical Properties of Graft Copolymer of Corn Starch and Acrylamide"—Y. Chen et al.—Polymer Composites—Vo. 28, 2007, pp. 47-56.

International Preliminary Report.

* cited by examiner

POLYSACCHARIDE MATRIX HAVING A GRAFTED POLYMER, METHOD FOR PRODUCING THE SAME AND USE THEREOF

BACKGROUND OF THE INVENTION

1. Field of the Invention

The present invention relates to a porous, non-particulate, convectively permeable polysaccharide matrix, on the surface of which there is fixed a grafted-on polymer derived from at least one ethylenic monomer compound having functional groups, wherein the polysaccharide matrix is prepared by grafting a porous, non-particulate, convectively permeable polysaccharide starting matrix with the at least one ethylenic monomer compound having functional groups in the presence of an organic acid having at least one carboxylic acid group and/or having at least one acidic XH group, where X=—O, —S, or —N, and of a transition metal or lanthanide compound, and also to processes for preparing the polysaccharide matrix and to the use of a polysaccharide matrix of this kind.

2. Description of the Related Art

The filtration, purification or removal of biomolecules such as proteins, amino acids, nucleic acids, viruses or endotoxins from liquid media is of great interest to the biopharmaceutical industry. Porous, non-particulate polysaccharide matrices, particularly in the form of adsorption membranes, are used especially in such processes in which the adsorbands are present in the liquid phase at very low concentrations in relation to the capacity of the matrix, and so, based on the unit area of the matrix, a large volume of the liquid phase can be processed until the capacity is exhausted. A typical application is the adsorption of deoxyribonucleic and ribonucleic acids (RNA and DNA), viruses, host cell proteins and endotoxins, in order to remove these contaminants from antibody-containing solutions using positively charged membranes.

The open pore structure of said membranes permits the adsorption of large adsorbands in the pore interior. For conventional gels, adsorption in these cases is limited to the outer particle surface. Therefore, membranes are used with success especially in the purification of large adsorbands such as DNA, RNA, blood coagulation factor VIII (FVIII) and viruses. However, for the adsorption of smaller adsorbands, the smaller inner surface of the membranes and the resulting lower capacity is disadvantageous compared to chromatography gels.

DE 39 29 648 C1 and EP 0 490 940 B1 disclose processes for grafting onto nitrogen-containing polymers, more particularly polyamides. They are based on the hydrogen of NH groups of the polymers being replaced by a halogen, preferably by a chlorine atom from organic hypohalites, organic N-halogen compounds or tetrachloromethane, and nitrogen free-radical formation is subsequently effected by reaction with a reducing agent. Any desired ethylenic monomers can then be grafted onto the free-radical nitrogen sites. The disadvantage of these membranes prepared according to these processes, which membranes have been proven to be useful per se, is that they have markedly lower hydraulic permeabilities than the starting membrane.

EP 0 527 992 B1 therefore proposes solving the problem of the reduced hydraulic permeability by coating membranes comprising a first polymer (e.g., cellulose hydrate, polyvinylidene difluoride (PVDF) or cellulose hydrate) with a solution of a second polymer, preferably an N-chlorinated nylon derivative, and subsequently grafting the membrane thus coated with ethylenic monomers. A disadvantage of this process is that the ethylenically unsaturated monomers cannot be grafted onto the first polymer directly and that the structural prerequisite for the grafting reaction is thus the coating of the first polymer with the solution of the second polymer before grafting can take place. This process is complicated and cost-intensive owing to the multiplicity of its individual steps.

Ion exchangers based on hydroxyl-containing supports (e.g., Fractogel® TSK from Merck), on the surface of which epoxy-containing methacrylic acid derivatives are grafted, are known from EP 0 722 360 B1. The epoxy groups of the grafted-on polymer can be subsequently converted to vicinal diol or 1,2-aminoalcohol functions by NH— or OH-containing reagents.

EP 0 337 144 B1 discloses hydroxyl-containing supports, the surface of which has covalently bonded to it polymers producible by graft polymerization which have the unit [—CR'R"—CR1Y]n, where Y=—CO2R4, —CN, —CHO, —OH, —CH2NH2 or —CH2NR2R3, as repeat unit. The supports are used for fractionating immunoglobulins in human serum and in murine ascitic fluid containing monoclonal antibodies.

EP 1 163 045 B1 discloses a process for preparing cationically modified membranes, wherein a microporous starting membrane, preferably comprising polyethersulphone, is provided with a coating prepared by crosslinking a composition comprising a diallylamine copolymer having epoxy groups and cationic groups, a polyalkyleneamine, and an amine-reactive compound having a cationic group. The amine-reactive compound is preferably a glycidyl compound having ammonium groups.

EP 1 614 459 B1 discloses a process for preparing cationically modified membranes, wherein a microporous starting membrane, preferably comprising (optionally hydrophilic) polyethersulphone, is treated with a mixture of a diallylamine copolymer, a diallyldialkylammonium halide and an acrylic acid monomer having quaternary ammonium groups, and is converted into the cationically modified membrane by heat treatment.

EP 0 538 315 B1 discloses a porous matrix consisting of a porous support having a sponge structure, which support has on its inner and outer surface a grafted-on polymer layer having functional groups, wherein the polymer layer is solvatable by a liquid phase in contact with the matrix such that it can occupy adjustable proportions of the pore volume of the porous support. Precursors used for the porous support are nitrogen-containing polymers, for example nylon derivatives or cellulose hydrate coated with nylon derivatives, onto which monomers, for example in the form of a mixture of hydroxyethyl methacrylate and glycidyl methacrylate, are grafted via N—Cl groups as reactive sites.

Y. Chen et al. disclose in "Polymer Composites", vol. 28, 2007, pages 47-56, the preparation of a graft copolymer from corn starch and acrylamide as a monomer to be grafted on in the presence of a mixture of cerium(IV) ammonium sulphate as grafting initiator and citric acid. According to IR spectroscopic studies by the authors, for efficient grafting onto the corn starch, oxidative ring cleavage of the hexose building blocks of the corn starch is essential, and subsequently, as a result of reaction with Ce4+ cations, free-radical carbon atoms are generated in the polymer backbone of the starch for the reaction with acrylamide.

EP 1 386 660 B1 discloses processes for isolating immunoglobulins from immunoglobulin mixtures in the pH range of from 2 to 10, wherein use is made of a matrix M-SP1-L, which has in each case a plurality of variable, functional groups SP1-L. Here, M is a chromatography starting matrix to which ligands L having a molecular weight not more than 500 daltons are bonded via spacers SP1. The ligands L are preferably selected from the group consisting of monocyclic or bicyclic (hetero)aromatic compounds, which may optionally carry acidic groups.

EP 0 921 855 B1 likewise discloses processes for isolating immunoglobulins from immunoglobulin mixtures in the pH range of from 2 to 10, wherein use is made of a matrix M to which the functional group SP1-L is bonded. The ligand L, which is bonded to the matrix M by means of a spacer SP1, is selected from the group consisting of benzimidazoles, benzothiazoles and benzoxazoles. The ligand L may optionally carry acidic groups, such as sulphonic or carboxylic acid substituents, on its bicyclic, heteroaromatic moiety.

EP 1 718 668 B1 discloses a process for separating antibodies from at least one contaminant in a solution, wherein use is made of a chromatography resin on which only multimodal ligands are immobilized. Here, multimodal ligands are ligands which can enter into at least two different binding interactions (i.e., an ionogenic and a hydrophobic interaction) with the components to be separated. The ligands have cation-exchanging groups and at least one (hetero)aromatic ring system for these two binding interactions.

An object of the present invention is to provide a porous, non-particulate, convectively permeable polysaccharide matrix, on the surface of which there is fixed a grafted-on polymer and which has a high protein binding capacity, and to provide cost-effective and efficient processes for preparing said polysaccharide matrix. A further object of the invention is to provide a novel use of the polysaccharide matrix for material separation.

SUMMARY OF THE INVENTION

The invention relates to a porous, non-particulate, convectively permeable polysaccharide matrix, on the surface of which there is fixed a grafted-on polymer derived from at least one ethylenic monomer compound having functional groups, which matrix is prepared by grafting a porous, non-particulate, convectively permeable polysaccharide starting matrix with the at least one ethylenic monomer compound having functional groups in the presence of an organic acid having at least one carboxylic acid group and/or having at least one acidic XH group, where X=—O, —S, or —N, and of a transition metal or lanthanide compound to generate a polymer having functional groups which is grafted onto the polysaccharide starting matrix.

In the context of the present invention, a porous, non-particulate polysaccharide matrix is understood to mean open-pored foams or microporous membranes which comprise a polysaccharide in each case. Preference is given to microporous membranes having a sponge-type structure which consist of a coherent spatial system of pores and therefore have a high specific surface area in proportion to their flow resistance. The typical layer thickness of the microporous membranes usable as polysaccharide matrix is in the range of between 50 and 500 µm, preferably between 100 and 300 µm. Mean pore sizes are preferably in the range from 0.01 to 20 µm, particularly preferably in the range from 0.1 to 15 µm, and most preferably in the range from 0.4 to 10 µm, with the mean pore size being determined using a "Capillary Flow Porometer 6.0" Coulter Porometer, CAPWIN Software System, Porous Materials Inc. Membranes of this kind can be planar or cylindrical. Cylindrical membranes are referred to as membrane hollow fibres, membrane capillaries or membrane tubes. Flat membranes are preferred in the context of the invention, with adsorption membranes integrated in spiral-wound or stack modules being particularly preferred.

DETAILED DESCRIPTION OF THE PREFERRED EMBODIMENTS

In the context of the present invention, a convectively permeable polysaccharide matrix is to be understood to mean a polysaccharide matrix in which the action of a hydraulic pressure difference is used to achieve convective permeation with an adsorband-containing medium, whereby, instead of purely diffuse transport of the adsorband(s) in the direction of a concentration gradient into the interior of the matrix, convective transport is achieved, which, provided the flow rate is high, is very much faster than diffusive transport.

As a result, a disadvantage inherent to the particulate matrices (e.g., chromatography gels) and referred to as diffusion limitation can be avoided. The disadvantage is that, with increasing particle size of the matrix and with increasing molar mass of the adsorband, the time required to achieve adsorption equilibrium increases considerably, and this results in worsening of the kinetics.

In a preferred embodiment, the polysaccharide starting matrix consists of polysaccharide, while, in a further embodiment, it is a porous support having a polysaccharide coating.

In these two embodiments, the polysaccharide is selected from the group consisting of cellulose esters, cellulose ethers, cellulose hydrate, agarose, chitin, chitosan, dextran or combinations thereof. Optionally, the aforementioned polysaccharides may be crosslinked.

Particularly preferred polysaccharides are cellulose esters, more particularly cellulose monoacetate, cellulose diacetate, cellulose triacetate, cellulose propionate, cellulose butyrate, cellulose acetobutyrate or cellulose nitrate, cellulose ethers, more particularly methylcellulose or ethylcellulose, and also mixtures thereof, with cellulose acetates, more particularly cellulose diacetate, being most preferred.

In the aforementioned embodiment of a porous support having a polysaccharide coating, the porous support is preferably microporous and consists of a polymer which is selected from the group consisting of polyamide, poly(ether) sulphone, polyvinylidene difluoride, polyacrylonitrile, polyvinyl chloride, polypropene, polyethene, polytetrafluoroethene, their copolymers or mixtures thereof.

On the surface of the porous polysaccharide matrix according to the invention, there is fixed a grafted-on polymer derived from at least one ethylenic monomer compound having functional groups, wherein surface of the porous matrix is understood to mean both the inner surface, i.e., the pore inner wall areas, and the outer surface, i.e., the outer areas of the porous matrix.

Preferably, the polymer grafted onto the polysaccharide starting matrix is formed from at least one ethylenic monomer compound which is a (meth)acrylic acid derivative and whose functional groups are ionogenic, or convertible-to-ionogenic, groups, hydrophobic groups and/or epoxy groups.

For the purposes of the present invention, preference is given especially to ethylenic monomer compounds selected from the group consisting of styrene, alpha-methylstyrene, 4-ethoxystyrene, 3,4-dimethoxystyrene, 4-benzyloxy-3- methoxystyrene, fluorostyrene, chloromethylstyrene, 4-tert-butylstyrene, vinylanisole, 4-vinylbenzoic acid, 4-vinylbenzyl chloride, vinylaniline, N,N-dimethylvinylbenzylamine, vinylbenzyl trimethylammonium chloride, 4-vinylbiphenyl, 2-vinylnaphthalene, N-(isobutoxymethyl)acrylamide, N-(butoxymethyl)acrylamide, N-tert-butylacrylamide, N,N-dimethylacrylamide, N-isopropylacrylamide, N-phenylacrylamide, N-[tris(hydroxymethyl)methyl]acrylamide, benzyl 2-propylacrylate, ethylene glycol phenyl ether acrylate, hexyl acrylate, isooctyl acrylate, tetrahydrofuryl acrylate, 2,2,3,3,4,4,5,5,6,6,7,7-dodecafluoroheptyl acrylate, benzyl methacrylate, butyl methacrylate, 3-chloro-2-hydroxypropyl methacrylate, cyclohexyl methacrylate, ethylene glycol phenyl ether methacrylate, 2-(methylthio)ethyl methacrylate, phenyl methacrylate, poly(propylene glycol) methacrylate, allyl benzyl ether, vinylpyridine, vinyl acetate, poly(ethylene glycol)(n)monomethacrylate or combinations thereof. These aforementioned monomers have hydrophobic groups as functional groups, which are also possessed by the polymer grafted onto the polysaccharide matrix.

In a further preferred embodiment of the membrane according to the invention, the preparation thereof makes use of at least one ethylenic monomer compound which comprises as functional groups ionogenic groups, or groups convertible into ions, preferably acidic groups. Preference is given especially to acrylic acid, methacrylic acid, 2-acrylamidoglycolic acid, 2-acrylamido-2-methyl-1-propanesulphonic acid, (3-acrylamidopropyl)trimethylammonium chloride, N,N-dimethylacrylamide, N-(3-dimethylaminopropyl) methacrylamide, [2-(acryloyloxy)ethyl]trimethylammonium chloride, diallyldimethylammonium chloride, 2-carboxyethyl acrylate, 2-(dimethylamino)ethyl acrylate, 2-aminoethyl methacrylate, 2-(diethylamino)ethyl methacrylate, [3-(methacryloylamino)propyl]dimethyl(3-sulphopropyl) ammonium hydroxide, [3-(methacryloylamino)propyl] trimethylammonium chloride, [3-(acryloylamino)propyl] trimethylammonium chloride, [2-(methacryloyloxy)ethyl] trimethylammonium chloride, 1-(3-sulphopropyl)-2-vinylpyridinium hydroxide, sulphoethyl(meth)acrylate, sulphopropyl(meth)acrylate, vinylsulphonic acid derivatives, styrenesulphonic acid derivatives or combinations thereof.

In a further embodiment, the membrane according to the invention is prepared using at least one ethylenic monomer compound which comprises as functional groups polar, nonionogenic groups, more particularly hydroxypropyl(meth) acrylate, 3-(meth)acryloylamino-1-propanol, 4-hydroxybutyl(meth)acrylate, 2-hydroxy-3-phenoxypropyl acrylate, 2-hydroxyethyl(meth)acrylate, glycerol monomethacrylate, vinylpyrrolidone, vinyl alcohol or combinations thereof.

A further preferred ethylenic monomer compound for the purposes of the present invention comprises as functional groups epoxy groups which can subsequently be reacted with nucleophiles. Particular preference is given to glycidyl acrylate and glycidyl methacrylate.

In a further embodiment of the invention, the membrane according to the invention is prepared from at least one ethylenic monomer compound which comprises as functional groups crosslinking-capable groups which, after the ethylenic monomer has been grafted onto the starting matrix, enable crosslinking of the grafted-on polymer to take place, for example ethylene glycol dimethacrylate, glycerol dimethacrylate, 1,4-butanediol diacrylate, diethylene glycol dimethacrylate, tetraethylene glycol dimethacrylate, poly (ethylene glycol)(n)diacrylate, poly(ethylene glycol)(n) dimethacrylate, 1,3-diisopropenylbenzene, bisphenol A dimethacrylate, allyl methacrylate, 3-(acryloyloxy)-2-hydroxypropyl methacrylate, 1,3-butanediol diacrylate, 1,4-butanediol diacrylate, 1,4-butanediol dimethacrylate, N,N'-methylenebisacrylamide, 1,3,5-triacryloylhexahydro-1,3,5-triazine, 1,1,1-trimethylolpropane triacrylate, poly(ethylene glycol) bisphenol A diglycidyl ether adducts or combinations thereof. These monomers having crosslinking-capable groups may be used either alone or in combination with at least one of the aforementioned monomer compounds to prepare the membrane according to the invention.

Furthermore, it is possible to graft onto the polysaccharide starting matrix all the aforementioned types of monomer compounds, in each case alone or in combination with at least one further variety, which can be any, of the aforementioned monomer compounds.

In a particularly preferred embodiment, the polysaccharide matrix according to the invention is prepared by grafting a mixture of glycidyl acrylate or glycidyl methacrylate with benzyl methacrylate.

Grafting of the aforementioned at least one ethylenic monomer compound onto the polysaccharide starting matrix is effected especially advantageously in the presence of a transition metal or lanthanide compound which generates free-radical sites on the starting matrix, onto which the at least one ethylenic monomer compound is grafted free-radically. Preferably, the membrane according to the invention is prepared by grafting in the presence of a transition metal or lanthanide compound from the group consisting of cerium, manganese, iron, nickel, cobalt, vanadium compounds or combinations thereof. Particular preference is given to using Ce(IV) salts.

It was found that, surprisingly, the polysaccharide matrix according to the invention has a significantly increased protein binding capacity when the grafting of the at least one ethylenic monomer compound onto the polysaccharide starting matrix is effected in the presence of an organic acid having at least one carboxylic acid group and/or at least one acidic XH group, where $X=$—O, —S, or —N. The static binding capacity for bovine serum albumin (BSA) in particular can be increased by up to 8.4-fold with respect to a comparative polysaccharide matrix in which all the preparation parameters are identical except for the use of this aforementioned organic acid.

Static binding capacity is to be understood here to mean the mass, bound at equilibrium, of an adsorband (e.g., BSA) with reference to the unit area of a polysaccharide matrix according to the invention present particularly preferably as a membrane, in mg/cm2.

The polysaccharide matrices according to the invention having static protein binding capacities increased by 1.5- to 8.4-fold over the above-mentioned comparative matrix can be prepared by the above-described grafting in the presence of an organic acid having at least one carboxylic acid group and/or at least one acidic XH group, wherein said organic acid is selected from the group consisting of citric acid, malic acid, tartaric acid, fumaric acid, maleic acid, succinic acid, oxalic acid, malonic acid, ascorbic acid, glucuronic acid, lactic acid or combinations thereof and where $X=$—O.

In one embodiment of the present invention, the functional groups of the polymer grafted onto the polysaccharide starting matrix per se may be capable of interacting with adsorbands present in fluids.

In a further, preferred embodiment of the invention, it is possible, after the grafting, for the functional groups of the polymer grafted onto the polysaccharide starting matrix to be reacted with at least one ligand which is capable of interacting with adsorbands in fluids.

Particularly preferably, the ligand has cationic, anionic and/or hydrophobic groups. The aforementioned ligand reacts with the functional groups of the monomer units of the grafted-on polymer, whereby each monomer unit is transformable into a repeat unit, functionalized by the at least one ligand, of the grafted-on polymer ("polymer analogous reaction" of the ligand).

Preferred ligands having a cationic group in the context of this invention are primary amines having one nitrogen atom, selected in particular from the group consisting of butylamine, hexylamine, cyclopropylamine, cyclohexylamine, aniline, chloroaniline, benzylamine, phenylethylamine, phenylpropylamine, phenylhexylamine, 2,3,4,5,6-pentafluoroaniline, 4-(trifluoromethyl)aniline, toluidine, 1-(4-methylphenyl)ethylamine, 1-naphthylamine, 1-methyl-3-phenylpropylamine or combinations thereof, secondary amines having one nitrogen atom, for example dimethylamine, N-ethylmethylamine, diisopropylamine, N-methylaniline, N-methylcyclohexylamine, 4-trifluoromethyl-N-methylaniline, N-benzylmethylamine, N-ethylaniline, N-methylethanolamine, 4-methoxy-N-methylaniline, N-ethylcyclohexylamine, N-ethylbenzylamine, 2-methoxy-N-methylbenzylamine, diphenylamine, N-cyclohexylaniline, dibenzylamine or combinations thereof, and tertiary amines having one nitrogen atom, selected from the group consisting of trimethylamine, N,N-dimethylethylamine, N,N-diethylmethylamine, N,N-dimethylbutylamine, N,N-dimethylhexylamine, N-methyldipropylamine, 6-(dimethylamino)fulvene, N,N-dimethylaniline, N,N-dimethylcyclohexylamine, N,N-dimethylbenzylamine, N,N-dimethyl-1-naphthylamine, N-hexylaniline, dicyclohexylamine, N-benzylaniline, N,N-dicyclohexylmethylamine, N-benzyl-N-ethylaniline, N-benzyl-N-hydroxyethyl-N-methylamine or combinations thereof.

A further group of ligands preferred in the context of this invention having more than one cationic group are amines having more than one nitrogen atom, referred to hereinafter as polyamines. By reacting the functional groups of the polymer grafted onto the polysaccharide starting matrix with the aforementioned polyamines, it is possible to crosslink the grafted-on polymer and to increase the density of positive charge carriers by quaternizing of the nitrogen atoms. Particularly preferably, polyamines are selected from the group consisting of ethylendiamine, 1,4-diaminobutane, 1,6-diaminohexane, 1,8-diaminooctane, N,N-dimethylethylenediamine, 3-(dimethylamino)-1-propylamine, diethylenetriamine, N,N'-dimethyl-1,3-propanediamine, N,N,N'-trimethylethylenediamine, 2-(aminomethyl)-2-methyl-1,3-propanediamine, 1,4-phenylenediamine, hexamethylenetetramine, N,N-diethylethylenediamine, N,N,N',N'-tetramethylethylenediamine, diethyldimethylpropanediamine, N,N,N'-trimethyl-1,3-propanediamine, triethylenetetramine, tris(2-aminoethyl)amine, 4-aminobenzylamine, N,N,N',N'-tetramethyl-1,3-propanediamine, 3,3'-diamino-N-methyldipropylamine, tris(dimethylamino)methane, 4-(2-aminoethyl)aniline, N,N-dimethyl-p-phenylenediamine, N-phenylethylenediamine, N,N'-dimethyl-1,6-hexanediamine, bis[2-(N,N-dimethylamino)ethyl]ether, tetraethylene-pentamine, polyethyleneimines of varied molecular weights between 500 and 500 000 g/mol, N-benzylethylenediamine, N-cyclohexyl-1,3-propanediamine, N,N,N',N'',N''-pentamethyldiethylenetriamine, N,N,N',N'-tetramethyl-p-phenylenediamine, 1,4-bis(3-aminopropoxy)butane, 4,4'-oxydianiline, 2-[2-(dimethylaminoethyl)methylamino]ethanol, piperazine, N-methylpiperazine, N,N-dimethylpiperazine, aminoethylpiperazine, 1,4-bis-(3-aminopropyl)piperazine, 1-(2-hydroxyethyl)piperazine, diazabicyclooctane, agmatine, S-triazine or combinations thereof.

When using the aforementioned ligands having one or more than one nitrogen atom, the polysaccharide matrix according to the invention is preferably prepared by grafting at least one ethylenic monomer compound which has as functional groups epoxy groups which enter a ring-opening reaction by reaction with the nitrogen atom(s) of the ligand. Particularly preferred as ethylenic monomer compounds in this embodiment are glycidyl acrylate and/or glycidyl methacrylate.

In the case of ligands having more than one nitrogen atom, it is possible to crosslink the grafted-on polymer of the polysaccharide matrix according to the invention by the ring-opening reaction of the epoxy groups by two or more of said nitrogen atoms, wherein said crosslinking can be effected intermolecularly with epoxy groups of two different grafted-on polymer chains or intramolecularly with epoxy groups of the same grafted-on polymer chain.

In a further variant of the invention in which use is made of polyamines having more than one nitrogen atom, particularly preferably two nitrogen atoms, as ligand, the ring-opening reaction of the epoxy groups is effected by only one of said nitrogen atoms, whereas the remaining nitrogen atom(s) not involved in the ring-opening reaction contribute(s) to increasing the density of ion-exchanging groups on the polysaccharide matrix according to the invention.

Particularly preferably, the polyamine used as ligand is a symmetrical or asymmetrical polyamine of the formula (I)

$$R^1R^2N\text{—}B\text{—}NR^3R^4 \qquad (I),$$

where it is possible to control via the length and structure of the bridge B whether only the group $R^1R^2N$ or else the group $NR^3R^4$ enters a ring-opening reaction with epoxy groups of the grafted-on polymer.

In the case of symmetrical polyamines, the groups $R^1R^2N$ and $NR^3R^4$ are identical, and the bridge B has a symmetrical structure, i.e., the bridge B has a mirror plane perpendicular to a notional axis running through the cyclic or acyclic molecular chain of the formula (I). The reactivity of the two amino groups is identical, whereby the probability of a dual ring-opening reaction of the epoxy groups by the $R^1R^2N$ and the group $NR^3R^4$ is increased. A reaction via only one of these two amino groups can be influenced by the length of the bridge B and the concentration of the diamine in the reaction liquor used. The shorter the bridge B and the higher the concentration of the diamine in the liquor, the greater the probability of a ring-opening reaction by only one of the groups $R^1R^2N$ or $NR^3R^4$. Alternatively, one of these amino groups can be protected by suitable protective groups from reacting with functional groups of the grafted-on polymer. Methods of introducing protective groups into amines are known to the person skilled in the art ("Protective Groups in Organic Synthesis", third edition, Theodora W. Greene, Peter G. M. Wuts, 1999).

Examples of symmetrical polyamines preferred for the purposes of the invention are, for example, N,N,N',N'-tetramethylethylenediamine, N,N,N',N'-tetramethyl-1,3-propanediamine, tetraethylenepentamine, pentaethylenehexamine, N,N,N',N'',N''-pentamethyldiethylenetriamine, bis[2-(N,N-dimethylamino)ethyl]ether, tetramethyl-1,6-hexanediamine, N,N'-dimethylpiperazine, 1,2-diaminocyclohexane, ortho- and/or para-xylylenediamine, N,N,N',N'-tetramethyl-1,4-butanediamine or 1,4-diazabicyclo[2.2.2]octane.

In the case of asymmetrical polyamines, the substituents of the $R^1R^2N$ and the $NR^3R^4$ group are different. This results in a differing reactivity of the two amino groups. As a result, the reaction of only one amino group $R^1R^2N$ or $NR^3R^4$ with the grafted-on polymer takes place preferentially.

Examples of asymmetrical diamines are, for example, 3-(dimethylamino)-1-propylamine, N,N,N'-trimethyl-1,3-propanediamine, 2-amino-5-diethylaminopentane, N,N-diethyl-N',N'-dimethyl-1,3-propanediamine, N,N-diethyl-N', N'-dimethyl-1,2-propanediamine, 2-{[2-(dimethylamino) ethyl]methylamino}ethanol, 1-(2-hydroxyethyl)piperazine or combinations thereof.

In a further embodiment of the present invention, use is made of a ligand which has at least one anionic group. Particular preference is given to ligands having sulphonic acid groups. These sulphonic acid ligands can, for example, be introduced into the membrane according to the invention by reaction of $SO_3^{2-}$ anions or their derivatives with the functional groups of the monomer units of the grafted-on polymer, whereby some or all monomer units can be transformed into a repeat unit, functionalized by a sulphonic acid group ($SO_3H$ group), of the grafted-on polymer. In this case, the functional group of the grafted-on monomer unit is preferably an epoxy group. Particularly preferably, the ethylenic monomer compound is glycidyl methacrylate.

According to a further preferred variant, it is possible, after the grafting, for the functional groups of the polymer grafted onto the polysaccharide starting matrix to be reacted with two different ligands, of which the first ligand has an anionic group and the second ligand has a hydrophobic group.

In this case, the functional groups of the grafted-on polymer are preferably epoxy groups which are reacted with the two different ligands in a ring-opening reaction. Particularly preferably, in this embodiment, the grafted-on polymer is formed from glycidyl methacrylate.

Particularly preferably, the first ligand is the sulphonic acid group —$SO_3H$, which can be introduced into the membrane as described above starting from $SO_3^{2-}$ ions or their derivatives, and the second ligand is aniline or sulphanilic acid (4-aminobenzenesulphonic acid) having a hydrophobic aryl moiety.

Most preferably, the first ligand is the sulphonic acid group and the second ligand is sulphanilic acid.

In the case of membranes according to the invention having this aforementioned ligand combination of sulphonic acid and sulphanilic acid groups, it was found that, surprisingly, they even have a high protein binding capacity at salt concentrations of up to 300 mM NaCl, whereas comparative membranes which were prepared under otherwise identical conditions, but only have sulphanilic acid as the sole ligand, have practically no protein binding capacity in the salt concentration range from 150 to 300 mM NaCl. This embodiment of the membrane according to the invention having sulphonic acid and sulphanilic acid ligands is therefore particularly suitable for use as a cation exchanger for contaminant removal and biomolecule concentration, for which processes cation exchangers were hitherto not usable because of their high salt sensitivity.

Adsorbands with which the at least one ligand is capable of interacting are to be understood in the context of this invention to mean one or more target substances and/or contaminants of biotechnological processes. The adsorbands can be individual molecules, associates or particles, in which case they are preferably proteins, nucleic acids, viruses, monoclonal antibodies or other substances of biological origin.

The interaction of the adsorbands with the ligands bonded to the polysaccharide matrix according to the invention may be reversible or irreversible; in either case, it enables the adsorbands to be removed from fluids, which are preferably aqueous liquids. Target substances are valuable materials which are to be recovered from the fluid in concentrated or pure form. Contaminants are materials whose removal from the fluid is necessary or desirable for technical, regulatory or other reasons. For the removal of contaminants, which is referred to as "negative adsorption", the adsorption can (may) proceed irreversibly when the polysaccharide matrix is to be used only once. In the case of the adsorption of the target substance(s), the process must proceed reversibly. Either a mere enrichment or a separation into two or more target substances can be carried out and, in the latter case, either the adsorption, the desorption or both can be effected selectively.

The polysaccharide matrices according to the invention are preferably prepared according to two alternative processes comprising, as common feature, the grafting of the at least one ethylenic monomer compound in the presence of the transition metal or lanthanide compound and in the presence of the organic acid.

The first process for preparing the polysaccharide matrix according to the invention comprises the following steps:

A) providing a porous polysaccharide starting matrix treated with an organic acid having at least one carboxylic acid group and/or at least one acidic XH group, where X=—O, —S or —N, and B) grafting the matrix provided in step A) with a mixture comprising a transition metal or lanthanide compound and at least one ethylenic monomer compound having functional groups to generate a polymer having functional groups which is grafted onto the polysaccharide starting matrix.

According to the invention, a polysaccharide starting matrix treated with the organic acid is provided in step A) by the organic acid selectively already being added to the casting solution for the preparation of the starting matrix or by essentially the entire surface of the porous starting matrix being contacted after its preparation with the organic acid. Preferably, said contacting is effected by dipping, spraying or impregnating the starting matrix with a solution of the organic acid in a suitable solvent, particularly preferably water or mixtures of water and organic solvents. The concentration of the organic acid based on the polysaccharide starting matrix is from 0.03 to 300 mmol of acid/kg of starting matrix, preferably from 0.1 to 100 mmol of acid/kg of starting matrix, and most preferably from 0.2 to 20 mmol of acid/kg of starting matrix.

The subsequent grafting in step B) is preferably carried out with a grafting liquor comprising the transition metal or lanthanide compound, the at least one ethylenic monomer compound and water or at least one organic solvent or emulsifier or mixtures thereof. The grafting liquor may be in the form of a solution or emulsion. The concentration of the transition metal or lanthanide compound in the grafting liquor is from 0.1 to 100 mmol/l, preferably from 0.5 to 50 mmol/l, and particularly preferably from 2 to 30 mmol/l. The concentration of the at least one ethylenic monomer compound in the grafting liquor is below 50% by weight, preferably below 20% by weight, and most preferably below 5% by weight.

According to one variant of said first process for preparing the polysaccharide matrix according to the invention, a porous polysaccharide starting matrix treated with the organic acid is provided in step A) and, subsequently, step B) is carried out with a grafting liquor comprising the monomer compound, the transition metal or lanthanide compound and additionally the organic acid. The concentration of the organic acid based on the polysaccharide starting matrix is from 0.01 to 300 mmol of acid/kg of starting matrix, preferably from 0.2 to 100 mmol of acid/kg of starting matrix, and most preferably from 0.3 to 20 mmol of acid/kg of starting matrix, whereas the concentration of the organic acid in the grafting liquor is between 0.01 and 100 mmol/l, preferably between 0.05 and 30 mmol/l, and most preferably between 0.1 and 3 mmol/l.

The concentration of the transition metal or lanthanide compound in the grafting liquor in this variant is from 0.1 to 100 mmol/l, preferably from 0.5 to 50 mmol/l, and particularly preferably from 2 to 30 mmol/l.

The second process for preparing the polysaccharide matrices according to the invention comprises the following steps:

A) providing a porous polysaccharide starting matrix treated with a transition metal or lanthanide compound, and B) grafting the matrix provided in step A) with a mixture comprising an organic acid having at least one carboxylic acid group and/or at least one acidic XH group, where X=—O, —S, or —N, and at least one ethylenic monomer compound having functional groups to generate a polymer having functional groups which is grafted onto the polysaccharide starting matrix.

According to the invention, a polysaccharide starting matrix treated with the transition metal or lanthanide compound is provided in step A) by essentially the entire surface of the porous starting matrix being contacted with the transition or lanthanide compound.

Preferably, said contacting is achieved by dipping, spraying or impregnating the starting matrix with a solution of the transition or lanthanide compound in a suitable solvent, particularly preferably water or mixtures of water and organic solvents. The concentration of the transition metal or lanthanide compound based on the polysaccharide starting matrix is from 0.2 to 500 mmol/kg of starting matrix, preferably from 1 to 200 mmol/kg of starting matrix, and most preferably from 2 to 100 mmol/kg of starting matrix.

The subsequent grafting in step B) is preferably carried out with a grafting liquor comprising the organic acid, the at least one ethylenic monomer compound and water or at least one organic solvent or mixtures thereof. The grafting liquor can be in the form of a solution or emulsion. The concentration of the organic acid in the grafting liquor is from 0.01 to 100 mmol/l, preferably from 0.05 to 30 mmol/l, and particularly preferably from 0.1 to 3 mmol/l.

The concentration of the at least one ethylenic monomer compound in the grafting liquor is below 50% by weight, preferably below 20% by weight, and most preferably below 5% by weight.

In the two aforementioned processes for preparing the polysaccharide matrix according to the invention, it is possible, after the grafting in step B), for the functional groups of the polymer grafted onto the polysaccharide starting matrix to be reacted in a subsequent step C) with at least one ligand which is capable of interacting with adsorbands present in fluids. Said ligand preferably has, as described above, cationic, anionic and/or hydrophobic groups and can enter a "polymer-analagous reaction" with the functional groups of the monomer units of the polymer grafted in step B), and so said monomer units are converted into repeat units, functionalized by the at least one ligand, of the grafted-on polymer. Alternatively, use can be made of two different ligands, of which the first ligand has an anionic group and the second ligand has a hydrophobic group.

In both processes according to the invention, the polysaccharide starting matrix is preferably selected from the group consisting of cellulose esters, cellulose hydrate, cellulose ethers, agarose, chitin, chitosan, dextran or combinations thereof.

Further variants of the two processes according to the invention for preparing the polysaccharide matrix according to the invention, in which variants cellulose esters are used as starting matrices, comprise an additional step of treatment of the polysaccharide matrix with a basic medium in order to hydrolyse ester groups of the polysaccharide matrix.

In one variant, in which the grafting step B) is followed by at least one ligand reacting with functional groups of the polymer in a further step C), the treatment of the polysaccharide matrix with the basic medium is carried out during or after step C).

In a further variant, in which the reaction with a ligand in step C) is omitted, the treatment of the wet or dried polysaccharide matrix with a basic medium is carried out after the grafting in step B).

The treatment with a basic medium is preferably carried out with an aqueous medium comprising an alkaline compound, particularly preferably an alkali metal hydroxide. Particular preference is given to aqueous solutions of sodium or potassium hydroxide. It is also possible to use mixtures of an alkali metal hydroxide and other alkaline compounds, such as alkali metal carbonates (e.g., sodium carbonate, potassium carbonate or caesium carbonate), trisodium phosphate and/or tripotassium phosphate.

The conditions for the basic treatment of the polysaccharide matrix are preferably selected such that any epoxy groups of the grafted-on polymer are not hydrolysed or only slightly hydrolysed. The concentration of the alkaline compound in the basic medium can be varied widely and is optimized such that the preservation of epoxy groups, the hydrolysis reaction of the ester groups of the matrix or the polymer-analagous reaction takes place preferentially. According to one particularly preferred embodiment of the present invention, use is made of a basic medium comprising water and sodium hydroxide, wherein the concentration of the sodium hydroxide in the solution is in a range from 0.1 to 10% by weight, particularly preferably in a range from 0.4 to 4% by weight.

The basic medium may comprise one or more additives. Suitable additives are especially salts, such as sodium chloride, sodium sulphate and sodium acetate, or organic solvents. The organic solvent is preferably selected from the group consisting of alcohols, ketones or ethers. Particular preference is given to ethanol, methanol, ethylene glycol, propylene glycol, glycerol, acetone, dioxane, N-methylpyrrolidone, diglyme or mixtures thereof.

The polysaccharide matrices according to the invention are used in material separation to remove particulate, colloidal and dissolved components from liquid media. The components to be removed are preferably undesired biological contaminants. Particularly preferably, the components to be removed comprise contaminants from cell culture solutions, for example cells, cell fragments, cell proteins, DNA, viruses, endotoxins. The removal comprises at least one of the undesired biological contaminants from the liquid medium, whereas target products likewise present in the liquid medium are isolated purified as an eluate. Target products for the purposes of the present invention are understood to mean biomolecules. Particularly preferably, target products are understood to mean proteins, oligopeptides, polypeptides or hormones. Liquid media are understood to mean all media which enable contacting of the constituents to be removed with the polysaccharide matrix according to the invention to be effected.

An advantage of the present invention is that suitable selection of the at least one ethylenic monomer compound and of the at least one ligand makes it possible to provide polysaccharide matrices having a high protein binding capacity for the particular material separation application desired.

EXAMPLES

The present invention is explained in more detail below by means of the examples, but without the examples limiting the invention in any way.

Any mention of a CA membrane in the examples refers to a type of cellulose acetate membrane which is reinforced with polyester non-woven and has a pore diameter of about 3 μm (measured using a "Capillary Flow Porometer 6.0" Coulter Porometer, CAPWIN Software System, Porous Materials Inc.) and a water flux of 600-700 ml/(min*bar*cm$^2$). All flux values for the membranes according to the invention and the comparative membrane are reported in ml/(min*bar*cm$^2$) for a 20 mM tris(hydroxymethyl)aminomethane/HCl (TRIS/HCl) buffer solution at pH=7.3. All static binding capacity values are reported in mg/cm$^2$.

The dynamic binding capacity in mg/ml is defined as the amount of absorband which has run (as solution) through the polysaccharide matrix according to the invention up to the time at which the concentration of the adsorband in the outflow of the polysaccharide matrix is a defined fraction of the concentration of the absorband in the inflow. For practical reasons, 10% of the inflow concentration is reported.

Unless otherwise specified, percentages are by weight.

Example 1

Grafting Glycidyl Methacrylate onto a CA Membrane Treated with an Organic Acid, Variant without Crosslinker, Lanthanide Compound in the Grafting Liquor 8 circular CA membrane sheets having a total area of 240 cm$^2$ were wetted with reverse-osmosis (RO) water, rinsed for 10 min with RO water, and then dipped for 10 min in 1000 g of a 0.1 mmol solution of an organic acid listed in table 1 in water. Afterwards, the membranes were dried for 15 min at 80° C. in a circulating air drying cabinet. 240 cm$^2$ of the CA membranes treated with the organic acid were secured in the gas space of a reaction vessel adjusted to a temperature of 22° C. 14.6 g of glycidyl methacrylate and 0.45 g of Arlatone® G (Atlas) were initially charged to the reaction vessel and gassed with nitrogen for 30 min together with the membranes. A solution comprising 1.5 g of Ce(IV) sulphate, 5.0 g of 20% strength sulphuric acid and 478 g of RO water was gassed with nitrogen for 30 min and transferred under nitrogen to the reaction vessel. The mixture was stirred for 5 min. Afterwards, the membranes from the gas space of the reaction vessel were dipped into the solution and, after about 5 s, were transferred back out of the solution to the gas space. After a further 20 min, the membranes were rinsed first for 5 min with 0.2% strength aqueous sulphuric acid and then for 10 min with running RO water. Afterwards, the membranes were shaken for 30 min in 0.5 M NaOH and rinsed for 10 min with running RO water.

Comparative Example 1

The comparative membrane of table 1 was prepared according to example 1, but before carrying out the grafting, no treatment of the CA membranes with one of the organic acids from table 1 was carried out.

Table 1 contains the data on flux and on capacity for bovine serum albumin for membranes grafted according to example 1 and reacted with quaternary ammonium groups according to example 5, compared to circular CA membrane sheets ("comparative membrane") which were not treated with an organic acid, but were otherwise reacted in the same way, firstly according to example 1 and then according to example 5. By using membranes treated with organic acid, it is possible to increase the static binding capacity for BSA by 1.5- to 8.4-fold compared to the comparative membrane, when the organic acid used is citric acid, malic acid, tartaric acid, fumaric acid, maleic acid, succinic acid, oxalic acid, malonic acid, ascorbic acid, D-glucuronic acid or lactic acid.

TABLE 1

| Organic acid | Flux [ml/(cm$^2$*min*bar)] | Capacity, bovine serum albumin (BSA) [mg/cm$^2$] |
|---|---|---|
| Citric acid | 51 | 2.85 |
| D-(+)-Malic acid | 70 | 2.29 |
| L-(−)-Malic acid | 51 | 2.22 |
| L-(+)-Tartaric acid | 97 | 1.87 |
| Tricarballylic acid | 401 | 0.30 |
| Fumaric acid | 242 | 0.70 |
| Maleic acid | 286 | 0.52 |
| Succinic acid | 257 | 0.75 |
| trans-Aconitic acid | 403 | 0.30 |
| cis-Aconitic acid | 404 | 0.34 |
| Oxalic acid | 151 | 1.22 |
| Malonic acid | 179 | 1.02 |
| L-(+)-Ascorbic acid | 121 | 1.23 |
| D-Glucuronic acid | 388 | 0.52 |
| Glycolic acid | 443 | 0.44 |
| DL-Lactic acid | 272 | 1.03 |
| 3-Hydroxy-2-butanone | 483 | 0.34 |
| 4-Hydroxy-3-hexanone | 459 | 0.32 |
| Comparative membrane | 368 | 0.34 |

Example 2

Grafting Glycidyl Methacrylate onto a CA Membrane Treated with an Organic Acid, Variant with Crosslinker, Lanthanide Compound in the Grafting Liquor 8 circular CA membrane sheets having a total area of 240 cm$^2$ were wetted with RO water, rinsed for 10 min with RO water, and then dipped for 10 min in 1000 g of a 0.1 mM solution of citric acid in water. Afterwards, the membranes were dried for 15 min at 80° C. in a circulating air drying cabinet. 240 cm$^2$ of CA membranes were secured in the gas space of a reaction vessel adjusted to a temperature of 22° C. 14.5 g of glycidyl methacrylate, 0.07 g of ethylene glycol dimethacrylate and 0.45 g of Arlatone® G (Atlas) were initially charged to the reaction vessel and gassed with nitrogen for 30 min together with the membranes. A solution comprising 1.5 g of Ce(IV) sulphate, 5.0 g of 20% strength sulphuric acid and 478 g of RO water was gassed with nitrogen for 30 min and transferred under nitrogen to the reaction vessel. The mixture was stirred for 5 min. Afterwards, the membranes from the gas space of the reaction vessel were dipped into the solution and, after about 5 s, were transferred back out of the solution to the gas space. After a further 20 min, the membranes were rinsed first for 5 min with 0.2% strength aqueous sulphuric acid and then for 10 min with running RO water. Subsequently, the membranes were shaken for 30 min in 0.5 M NaOH and rinsed for 10 min with running RO water.

Example 3

Grafting Glycidyl Methacrylate onto a CA Membrane Treated with a Lanthanide Compound, Variant with Crosslinker, Organic Acid in the Grafting Liquor 8 circular CA membrane sheets having a total area of 240 cm² were wetted with RO water, rinsed for 10 min with RO water, and dipped for 5 min in 500 g of a solution comprising 1.5 g of cerium(IV) sulphate, 5.0 g of 20% strength sulphuric acid and 478 g of RO water. Afterwards, the membranes were dried for 15 min at 60° C. in a circulating air drying cabinet. 240 cm² of CA membrane were secured in the gas space of a reaction vessel adjusted to a temperature of 22° C. A solution comprising 10.0 g of glycidyl methacrylate, 0.05 g of ethylene glycol dimethacrylate, 0.05 g of citric acid and 490 g of RO water was, together with the membranes in the gas space of the reaction vessel, gassed with nitrogen for min. Afterwards, the membranes from the gas space of the reaction vessel were dipped into the solution and, after about 5 s, were transferred back out of the solution to the gas space. After a further 20 min, the membranes were shaken for 10 min in 500 g of 0.2% strength sulphuric acid. Subsequently, the membranes were rinsed for 10 min with running RO water. Afterwards, the membranes were shaken for 30 min in 0.5 M NaOH and rinsed for 10 min with running RO water.

Example 4

Grafting Two Different Monomers (Glycidyl Methacrylate and Benzyl Methacrylate) onto a CA Membrane Treated with an Acid, Variant with Crosslinker, Lanthanide Compound in the Grafting Liquor 8 circular CA membrane sheets having a total area of 240 cm² were wetted with RO water, rinsed for 10 min with RO water, and then dipped for 10 min in 1000 g of a 0.1 mM solution of citric acid in water. Afterwards, the membranes were dried for 15 min at 80° C. in a circulating air drying cabinet. 240 cm² of CA membranes were secured in the gas space of a reaction vessel adjusted to a temperature of 22° C. 13.5 g of glycidyl methacrylate, 0.07 g of ethylene glycol dimethacrylate, 1.0 g of benzyl methacrylate and 0.45 g of Arlatone® G (Atlas) were initially charged to the reaction vessel and gassed with nitrogen for 30 min together with the membrane. A solution comprising 1.5 g of Ce(IV) sulphate, 5.0 g of 20% strength $H_2SO_4$ and 478 g of RO water was gassed with nitrogen for 30 min and transferred under nitrogen to the reaction vessel. The mixture was stirred for 5 min. Afterwards, the membranes from the gas space of the reaction vessel were dipped into the solution and, after about 5 s, were transferred back out of the solution to the gas space. After a further 20 min, the membranes were rinsed for 10 min with running RO water. Afterwards, the membranes were shaken for 30 min in 0.5 M NaOH and rinsed for 10 min with running RO water.

Example 5

Polymer-Analagous Reaction to Introduce a Ligand (Quaternary Ammonium Group)

The grafted membranes from examples 1, 2 and 3 were treated successively with a 10% strength aqueous solution of trimethylamine for 35 minutes at 30° C. and with 5% strength aqueous sulphuric acid solution for 5 minutes at room temperature and then rinsed with running water for 10 minutes.

Example 6

Polymer-Analagous Reaction to Introduce a Ligand (Sulphonic Acid Group)

The membranes from example 1 were adjusted in a solution comprising 380 g of $Na_2SO_3$, 40.0 g of $Na_2HPO_4.H_2O$, 100 g of tetrabutylammonium bisulphate and 1200 g of water to a pH of 8.0 with 32% strength aqueous sodium hydroxide solution, treated for 45 min at 80° C., and then rinsed for 10 minutes with running water, for 5 minutes with 35 g of 1% strength aqueous hydrochloric acid, for 2×5 min with 30 g of aqueous 1M NaCl solution each time, for 5 min with 500 g of 5% strength aqueous sulphuric acid and for 10 minutes with running water.

Example 7

Polymer-Analagous Reaction to Introduce Two Different Ligands (Sulphonic Acid Group and Phenylamino Group)

312 g of an aqueous solution comprising 18% by weight of $Na_2SO_3$, 1% by weight of aniline, 5% by weight of tetrabutylammonium bisulphate, 2% by weight of $Na_2HPO_3.2H_2O$ (adjusted to pH 8 with 32% strength NaOH) were heated to 35° C. The membranes from example 1 were added, and the reaction solution was stirred for 16 h at 35° C. The membranes were then rinsed for 10 minutes with running RO water, for 15 minutes with 200 g of 5% strength aqueous sulphuric acid, for 2×10 minutes with 200 g of 50 mM aqueous $Na_2SO_4$ solution, for 5 minutes with running RO water, for 2×10 minutes with 300 g of ethanol and finally for 5 minutes with running RO water.

Example 8

Polymer-Analagous Reaction to Introduce a Ligand (Sulphonic Acid Group)

The membranes from example 2 were reacted as described in example 6.

Comparative Example 2

Polymer-Analagous Reaction to Introduce a Ligand (Sulphanilic Acid Group)

A 2% strength solution of sulphanilic acid (4-aminobenzenesulphonic acid) in RO water was adjusted to a pH of 11.3 with 32% strength NaOH. The membranes from example 2 were added, and the reaction solution was stirred for 3 h at 65° C. The membranes were rinsed for 10 minutes with running RO water, for 15 minutes with 200 g of 5% strength aqueous sulphuric acid, for 2×10 minutes with 200 g of 50 mM aqueous $Na_2SO_4$ solution, for 5 minutes with running RO water, for 2×10 minutes with 300 g of ethanol and finally for 25 minutes with running RO water.

Example 9

Polymer-Analagous Reaction to Introduce Two Different Ligands (Sulphonic Acid Group and Sulphanilic Acid Group)

The sulphonation solution described in example 6 was diluted with RO water to ⅔ of the starting concentration of the dissolved constituents and then admixed with sulphanilic acid (Aldrich S5263) until the sulphanilic acid content in the diluted sulphonation solution was 2% by weight or 4% by weight. After the sulphanilic acid had dissolved, the pH was adjusted to 11.3 with 32% strength NaOH. The membranes from example 2 were added, and the reaction solution was stirred for 3 h at 65° C. The membranes were rinsed for 10 minutes with running RO water, for 15 minutes with 200 g of 5% strength aqueous sulphuric acid, for 2×10 minutes with 200 g of 50 mM aqueous $Na_2SO_4$ solution, for 5 minutes with running RO water, for 2×10 minutes with 300 g of ethanol and finally for 25 minutes with running RO water.

Example 10

Polymer-Analagous Reaction to Introduce Quaternary Ammonium Groups with Crosslinking of the Grafted-on Polymer The membranes according to example 1 were treated for 35 minutes at 30° C. in an aqueous solution comprising 10% by weight of trimethylamine and 2.5% by weight of diazabicyclooctane and for 5 minutes at room temperature in 5% strength sulphuric acid and then rinsed for 10 minutes with running water.

Example 11

Polymer-Analagous Reaction to Introduce a Ligand Having a Secondary and Tertiary Amino Group The membranes from example 1 were treated for 1 h at 60° C. in a 20% strength aqueous solution of N-diethyl-N'-dimethyl-1,3-propanediamine and for 5 minutes at room temperature in 5% strength sulphuric acid and then rinsed for 10 minutes with running water.

Example 12

Polymer-Analagous Reaction to Introduce a Ligand Having a Tertiary Amino Group

The membranes from example 2 were treated successively for 1 h at 60° C. in a 1% strength aqueous solution of N,N-dimethylbenzylamine and for 5 minutes at room temperature in 5% strength sulphuric acid and then rinsed for 10 minutes with running water.

Evaluating the Membranes:

The membranes obtained were evaluated as described below.

1) Flux Determination

Membranes having an active membrane area of 12.5 $cm^2$ were each fitted into a casing and the time was measured to filter 100 ml of buffer (mixture comprising 10 mM KPi buffer (0.01 mol/liter potassium phosphate buffer having pH=7.0, which was prepared by mixing $KH_2PO_4$ solution with $K_2HPO_4$ solution) and 1 M aqueous NaCl solution, adjusted to a pH of 7.0). The flux values displayed in table 2 for the membranes reacted with ligands relate to the corresponding TRIS/HCl buffer at pH=7.3. The same buffers were used as for the binding capacity determinations described below.

2) Determining the Static Binding Capacity of Positively Charged Membranes Having Amine Ligands Membranes having an active membrane area of 17.6 $cm^2$ in each case were shaken in 35 ml of 20 mM TRIS/HCl (pH 7.3) for 3×5 min at about 80 revolutions per minute (rpm). Afterwards, the membranes were shaken in 35 ml of a solution of 2 mg/ml bovine serum albumin (BSA) solution (Kräber, Ellerbeck, order no. 041 80 10 900, lot no. 49 09 20 52) in 20 mM TRIS/HCl (pH=7.3) for 12-18 hours at 20-25° C. at about 80 rpm. Subsequently, the membranes were rinsed for 2×15 minutes with, in each case, 35 ml of 20 mM TRIS/HCl (pH=7.3). Afterwards, the membrane samples were shaken in 20 ml of a mixture comprising a solution of 20 mM TRIS/HCl and 1 M aqueous sodium chloride solution at pH=7.3. The amount of the eluted bovine serum albumin was determined by measuring the optical density (OD) at 280 nm.

3) Determining the Static Binding Capacity of Negatively Charged Membranes Having a Sulphonic Acid and/or Sulphanilic Acid Ligand According to Examples 6, 7, 8 and 9 and Comparative Example 2

Membranes having an active membrane area of 17.6 $cm^2$ in each case were shaken in 35 ml of 10 mM KPi buffer (pH 7.0) for 3×5 minutes at about 80 rpm. Afterwards, the membranes were shaken in 35 ml of a solution of 2 mg/ml lysozyme (Sigma Aldrich Chemie, Taufkirchen, order no. L6876, lot no. 114K0626) in 10 mM KPi buffer (pH 7.6) for 12-18 hours at 20-25° C. at about 80 rpm. Subsequently, the membranes were rinsed for 2×15 minutes with, in each case, 35 ml of 10 mM KPi buffer (pH 7.0). Afterwards, the membranes were shaken in 20 ml of a mixture comprising 10 mM KPi buffer and aqueous 1M sodium chloride solution (pH=7.3). The amount of the eluted lysozyme was determined by measuring the optical density (OD) at 280 nm.

4) Determining the Static Binding Capacities of Negatively Charged Membranes According to Examples 8 and 9 and According to Comparative Example 2 at the Different Concentrations of 150 Mm and 300 mM NaCl The static binding capacities of membranes according to comparative example 2 and according to examples 8 and 9 were determined according to the following method: Membranes having an active membrane area of 17.6 $cm^2$ in each case were shaken in 35 ml of 20 mM acetate buffer (pH=5.0, selectively adjusted to a NaCl concentration of 150 mM or 300 mM) for 3×5 minutes at about 80 revolutions/min. Afterwards, the membranes were shaken in 35 ml of a solution of 1 mg/ml globulin G-5009 Sigma (Sigma Aldrich Chemie, source: bovine blood) in 20 mM acetate buffer (pH=5.0, selectively adjusted to a NaCl concentration of 150 mM or 300 mM) for 12-18 hours at 20-25° C. at about 80 revolutions/min. Subsequently, the membranes were treated for 2×15 minutes with, in each case, 35 ml of 20 mM acetate buffer (pH=5.0, selectively adjusted to a NaCl concentration of 150 mM or 300 mM). Afterwards, the membranes were shaken in each case in 20 ml of a 20 mM acetate buffer (pH=5.0+1 M NaCl). The amount of the eluted globulin was determined by measuring the optical density (OD) at 280 nm.

5) Determining the Dynamic Binding Capacity of Positively Charged Membranes Having Amine Ligands 3 layers of membrane were clamped into a membrane holder. The membrane stack had a membrane area of 15 $cm^2$, a flow area of 5 $cm^2$ and a bed height (thickness of the membrane stack) of 750 μm in the membrane holder. The membranes in the membrane holder were flooded with 20 mM TRIS/HCl buffer (pH=7.3) in order to displace air and then connected to an "Äkta® Explorer 100" FPLC system from General Electric Health Care.

Afterwards, the membranes, or the membrane stack, were tested with respect to BSA (bovine serum albumin) binding using a test program comprising two steps. The two steps of the test program are specified below:

1. equilibration of the membranes with 10 ml of a 50 mM 20 mM TRIS/HCl buffer at pH=7.3

2. loading the membrane with 1 mg/ml BSA in 20 mM TRIS/HCl buffer at pH=7.3, until the concentration in the UV detector is 10% of the starting concentration.

Both steps were carried out at a flow velocity of 10 ml/min. In all the steps, the absorbance at 280 nm was measured in the UV detector beyond the membrane unit. The area above the breakthrough curve thus plotted was integrated after substrating the dead volume and hence the dynamic binding capacity at 10% breakthrough was calculated.

Table 2 below contains data on membranes according to the invention in which the functional groups of the grafted-on polymer are reacted with ligands. The entry "Example 1, 5" means, for example, that starting membranes were first reacted according to example 1 and subsequently further reacted with a ligand according to example 5.

TABLE 2A

| Membrane, polymer-analagous reaction | Thickness [μm] | Flux [ml/(min*bar*cm$^2$)] | [cm/h]* |
|---|---|---|---|
| 1) Example 1, 5 | 205 | 51 | 63 |
| 2) Example 1, 6 | 210 | 87 | 110 |
| 3) Example 1, 7 | 205 | 138 | 170 |
| 4) Example 1, 10 | 205 | 112 | 138 |
| 5) Example 1, 11 | 205 | 65 | 80 |
| 6) Example 2, 5 | 210 | 104 | 131 |
| 7) Example 2, 12 | 205 | 50 | 62 |
| 8) Example 3, 5 | 210 | 115 | 145 |
| 9) Example 4, 5 | 215 | 81 | 104 |

TABLE 2B

| Membrane, polymer-analagous reaction | Capacity [mg/cm$^2$] | [mg/ml]$^+$ | 10% DBC** [mg/cm$^2$] | [mg/ml]$^+$ |
|---|---|---|---|---|
| 1) Example 1, 5 | 2.85 | 139 | 2.15 | 105 |
| 2) Example 1, 6 | 1.77 | 84 | — | — |
| 3) Example 1, 7 | 2.62 | 128 | — | — |
| 4) Example 1, 10 | 2.22 | 108 | — | — |
| 5) Example 1, 11 | 2.28 | 111 | 1.73 | 84 |
| 6) Example 2, 5 | 2.35 | 112 | — | — |
| 7) Example 2, 12 | 2.64 | 129 | — | — |
| 8) Example 3, 5 | 2.05 | 98 | — | — |
| 9) Example 4, 5 | 2.03 | 94 | 1.68 | 78 |

Figure 1:
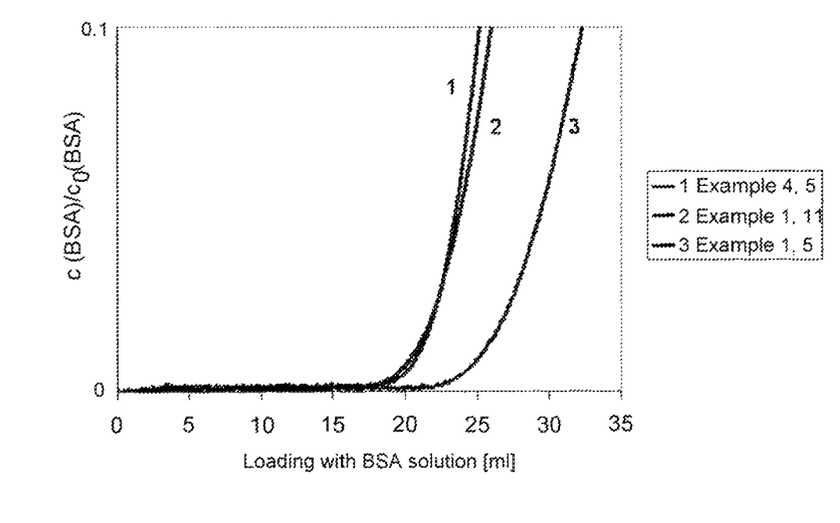
FIG. 1 is a graph showing breakthrough curves for bovine serum albumin for membranes prepared in accordance with entries 1, 5 and 9 of Table 2B.

*Flux through a membrane stack having a flow area of 1 cm$^2$ and a height of 1 cm at 1 bar measured using 20 mM TRIS/HCl buffer at pH = 7.3
**10% DBC = dynamic binding capacity at 10% breakthrough
$^+$Conversion of the capacity based on the membrane area in cm$^2$ into the capacity based on the membrane volume in ml, taking account of the membrane thickness FIG. 1 shows breakthrough curves for bovine serum albumin for membranes which were prepared according to entries 1), 5) and 9) of table 2B). The Y-axis shows the ratio between the concentration c(BSA) in the outflow and the concentration $C_0$(BSA) in the inflow, whereas the X-axis shows the loading with BSA.

Table 3 below contains data for the membrane according to comparative example 2 and for the membranes in accordance with the invention according to examples 8 and 9, which have at least one ligand having an anionic group. The membranes of comparative example 2, which only have the sulphanilic acid ligands, show only very low static binding capacities for globulin and for lysozyme, whereas membranes which have both sulphonic acid and sulphanilic acid groups as ligands exhibit a high static binding capacity for lysozyme and globulin, even at high salt concentrations.

TABLE 3A

| | Flux* [ml/(min bar cm$^2$)] | Globulin capacity [mg/cm$^2$] 150 mM NaCl | 300 mM NaCl |
|---|---|---|---|
| Example 8 | 50 | 1.17 | 0.09 |
| Comparative example 2 | 330 | 0.05 | 0.02 |
| Example 9 $C_0$** = 2% by weight Sulphanilic acid | 50 | 2.13 | 0.43 |
| Example 9 $C_0$** = 4% by weight Sulphanilic acid | 40 | 2.40 | 0.90 |

TABLE 3B

| | Thickness [μm] | Lysozyme capacity [mg/cm$^2$] |
|---|---|---|
| Example 8 | 210 | 2.32 |
| Comparative example 2 | 210 | 0.07 |
| Example 9 $C_0$** = 2% by weight Sulphanilic acid | 215 | 2.51 |
| Example 9 $C_0$** = 4% by weight Sulphanilic acid | 210 | 2.66 |

*Flux measured using 20 mM acetate buffer pH = 5.0 + 150 mM NaCl
**Concentration of sulphanilic acid in % by weight in the sulphonation solution according to example 9

The invention claimed is:

1. A porous polysaccharide matrix comprising:
a starting matrix selected from the group consisting of a polysaccharide matrix and a porous support having a polysaccharide matrix coating; and
grafted onto the starting matrix, a transition metal or lanthanide compound and an ethylenic monomer compound having functional groups;
wherein the ethylenic monomer compound was grafted onto the starting matrix in the presence of an organic acid having at least one carboxylic acid group and at least one acidic X—H group, where X=O, S, or N;
wherein the porous polysaccharide matrix has a static protein binding capacity that is 1.5 to 8.4 times a static protein binding capacity of a comparative matrix that was prepared by grafting in the absence of the organic acid having at least one carboxylic acid group and at least one acidic X—H group, where X=O, S, or N.

2. The porous polysaccharide matrix as claimed in claim 1, wherein the starting matrix consists of the polysaccharide matrix.

3. The porous polysaccharide matrix as claimed in claim 1, wherein the starting matrix consists of the porous support having a polysaccharide matrix coating.

4. The porous polysaccharide matrix as claimed in claim 3, wherein the porous support consists of a polymer selected from the group consisting of a polyamide, a poly(ether)sulphone, a polyvinylidene difluoride, a polyacrylonitrile, a polyvinyl chloride, a polypropylene, a polyethylene, a polytetrafluoroethylene, a copolymer thereof, and a mixture thereof.

5. The porous polysaccharide matrix as claimed in claim 1, wherein the starting-polysaccharide matrix and the polysaccharide coating are individually selected from the group consisting of a cellulose ester, a cellulose ether, a cellulose hydrate, agarose, chitin, chitosan, dextran, or a mixture thereof.

6. The porous polysaccharide matrix as claimed in claim 1, wherein the ethylenic monomer compound is a (meth)acrylic acid derivative and the functional groups of the ethylenic monomer compound are at least one of ionogenic, hydrophobic and epoxy groups.

7. The porous polysaccharide matrix as claimed in claim 1, wherein the organic acid is selected from the group consisting of citric acid, malic acid, tartaric acid, fumaric acid, maleic acid, succinic acid, oxalic acid, malonic acid, ascorbic acid, glucuronic acid, lactic acid, and a mixture.

8. The porous polysaccharide matrix as claimed in claim 1, further comprising a ligand that is capable of interacting with adsorbands present in fluids; wherein the functional groups are functionalized with the ligand.

9. The porous polysaccharide matrix as claimed in claim 8, wherein the ligand comprises at least one of cationic, anionic and hydrophobic groups.

10. The porous polysaccharide matrix as claimed in claim 9, wherein the functional groups are functionalized with a first ligand which comprises an anionic group and a second ligand which comprises a hydrophobic group.

11. The porous polysaccharide matrix as claimed in claim 10, wherein the first ligand comprises a sulphonic acid group or a group transformable into a sulphonic acid group and wherein the second ligand is aniline or 4-aminobenzenesulphonic acid.

12. The porous polysaccharide matrix as claimed in claim 8, wherein the ligand is a polyamine.

13. A process for preparing the porous polysaccharide matrix as claimed in claim 1, comprising the steps:
A) providing the starting matrix treated with an organic acid having at least one of at least one carboxylic acid group and at least one acidic XH group, where X=—O, —S or —N, and
B) grafting the matrix provided in step A) with a mixture comprising a transition metal or lanthanide compound and at least one ethylenic monomer compound having functional groups to generate a polymer having functional groups that is grafted onto the starting matrix.

14. A process for preparing the porous polysaccharide matrix as claimed in claim 1, comprising the steps:
A) providing the starting matrix treated with a transition metal or lanthanide compound, and
B) grafting the matrix provided in step A) with a mixture comprising an organic acid having at least one carboxylic acid group and/or at least one acidic XH group, where X=—O, —S, or —N, and at least one ethylenic monomer compound having functional groups to generate a polymer having functional groups which is grafted onto the polysaccharide starting matrix.

15. The process as claimed in claim 14, wherein, after the grafting in step B), the functional groups of the polymer grafted onto the polysaccharide starting matrix are reacted in a subsequent step C) with at least one ligand which is capable of interacting with adsorbands present in fluids.

16. The process as claimed in claim 14, wherein the polysaccharide is selected from the group consisting of cellulose esters, cellulose hydrate, cellulose ethers, agarose, chitin, chitosan, dextran and/or combinations thereof.

17. The process as claimed in claim 16, wherein the polysaccharide is a cellulose ester and the matrix is additionally treated with a basic medium either after step B), during step C) or after step C).

18. The porous polysaccharide matrix as claimed in claim 1, wherein the ethylenic monomer compound comprises a mixture of glycidyl acrylate or glycidyl methacrylate with benzyl methacrylate.

19. The porous polysaccharide matrix as claimed in claim 1, wherein the ethylenic monomer compound includes a methacrylate.

* * * * *